(12) United States Patent
Gong et al.

(10) Patent No.: US 12,089,996 B2
(45) Date of Patent: Sep. 17, 2024

(54) METHODS FOR ULTRASOUND SYSTEM INDEPENDENT ATTENUATION COEFFICIENT ESTIMATION

(71) Applicant: Mayo Foundation for Medical Education and Research, Rochester, MN (US)

(72) Inventors: Ping Gong, Rochester, MN (US); Pengfei Song, Champaign, IL (US); Shigao Chen, Rochester, MN (US); Joshua D. Trzasko, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 15 days.

(21) Appl. No.: 16/625,910

(22) PCT Filed: Jun. 22, 2018

(86) PCT No.: PCT/US2018/038951
§ 371 (c)(1),
(2) Date: Dec. 23, 2019

(87) PCT Pub. No.: WO2018/237244
PCT Pub. Date: Dec. 27, 2018

(65) Prior Publication Data
US 2020/0146656 A1    May 14, 2020

Related U.S. Application Data (60) Provisional application No. 62/524,043, filed on Jun. 23, 2017.

(51) Int. Cl.
*A61B 8/08* (2006.01)
*G01N 29/46* (2006.01)
*G01S 15/89* (2006.01)

(52) U.S. Cl.
CPC .......... *A61B 8/5223* (2013.01); *G01N 29/46* (2013.01); *G01S 15/892* (2013.01); *G01N 2291/015* (2013.01); *G01N 2291/02475* (2013.01)

(58) Field of Classification Search
CPC ................. A61B 8/5223; G01N 29/46; G01N 2291/02475; G01N 2991/015; G01S 15/892
See application file for complete search history.

(56) References Cited

U.S. PATENT DOCUMENTS

| | | | |
|---|---|---|---|
| 4,414,850 A | | 11/1983 | Miwa |
| 5,097,836 A | * | 3/1992 | Yamada ................ G01S 7/5206 600/443 |

(Continued)

OTHER PUBLICATIONS

T. Mo et al., "Calculations of Radar Backscattering Coefficient of Vegetation-Covered Soils," Remote Sensing of Environment, vol. 15, pp. 119-133, 1984 (Year: 1984).*

(Continued)

*Primary Examiner* — Joel Lamprecht
*Assistant Examiner* — Nyrobi Celestine
(74) *Attorney, Agent, or Firm* — Quarles & Brady LLP (57) ABSTRACT

Systems and methods for estimating acoustic properties in a region-of-interest in a subject or other object being imaged using a reference frequency method ("RFM") is described. Using this RFM technique, ultrasound data acquired at a given frequency are normalized by ultrasound data acquired at different frequencies (e.g., adjacent frequencies or otherwise) in order to provide estimations of the acoustic properties (e.g., attenuation coefficient, a backscatter coefficient, or both) that are independent of the ultrasound system used to acquire the underlying data. For instance, the amplitude of each frequency component can be normalized by a different frequency in the power spectrum to cancel out the system- (Continued)

dependent effects. Because the methods described in the present disclosure are system independent, they can be applied to any transducer geometry (e.g., linear or curved arrays) and using any beam pattern (e.g., focused or unfocused).

25 Claims, 5 Drawing Sheets

(56) References Cited

U.S. PATENT DOCUMENTS

| | | | | |
|---|---|---|---|---|
| 6,743,174 | B2* | 6/2004 | Ng | A61B 8/467 600/437 |
| 8,679,019 | B2* | 3/2014 | Jurvelin | A61B 8/0858 600/442 |
| 11,166,699 | B2* | 11/2021 | Labyed | G01S 7/52042 |
| 2009/0143681 | A1 | 6/2009 | Jurvelin | |
| 2010/0036292 | A1* | 2/2010 | Darlington | A61N 7/00 601/2 |
| 2010/0249590 | A1* | 9/2010 | Kanayama | G01S 15/8963 600/442 |
| 2013/0035594 | A1* | 2/2013 | Eda | A61B 8/469 600/442 |
| 2014/0114189 | A1 | 4/2014 | Kanayama | |
| 2017/0258453 | A1* | 9/2017 | Takayama | A61B 8/488 |
| 2017/0273667 | A1* | 9/2017 | Labyed | A61B 8/485 |
| 2018/0220997 | A1 | 8/2018 | Song | |

OTHER PUBLICATIONS

E. J. Boote et al., "Instrument-Independent Acoustic Backscatter Coefficient Imaging," Ultrasonic Imaging, vol. 10, pp. 121-138, 1988 (Year: 1988).*
K. A. Wear et al., "Measurements of ultrasonic backscatter Coefficients in human liver and kidney in vivo," Journal of the Acoustical Society of America, vol. 98, No. 4, pp. 1852-1857, Oct. 1995 (Year: 1995).*
R. J. Lavarello et al., "On the estimation of backscatter coefficients using single-element focused transducers," Journal of the Acoustical Society of America, vol. 129, No. 5, pp. 2903-2911, May 2011 (Year: 2011).*
J. R. Cook et al., "Tissue-mimicking phantoms for photoacoustic and ultrasonic imaging," Optical Society of America, vol. 2, No. 11, pp. 3193-3206 Oct. 2011 (Year: 2011).*
K. Nam et al., "Ultrasonic Attenuation and Backscatter Coefficient Estimates of Rodent-Tumor-Mimicking Structures: Comparison of Results among Clinical Scanners," Ultrasonic Imaging, vol. 33, No. 4, pp. 233-250, Oct. 2011 (Year: 2011).*
D. P. O'Leary et al., "Variable projection for nonlinear least squares problems," Computational Optimization and Applications, vol. 54, pp. 579-593, Apr. 2013 (Year: 2013).*
J. D. Evans et al., "Prospects for in vivo estimation of photon linear attenuation coefficients using postprocessing dual-energy CT imaging on a commercial scanner," Medical Physics, vol. 40, No. 12, pp. 121914-1-121914-16, Dec. 2013 (Year: 2013).*
K. Samimi et al., "Lower Bound on Estimation Variance of the Ultrasonic Attenuation Coefficient Using the Spectral-Difference Reference-phantom Method," Ultrasonic Imaging, vol. 39, No. 3, pp. 151-171, Oct. 2016 (Year: 2016).*
F. L. Lizzi et al., "Tissue Signature Characterization Utilizing Frequency Domain Analysis," 1976 Ultrasonics Symposium, pp. 714-719, 1976 (Year: 1976).*
M. O'Donnell, "Effects of Diffraction on Measurements of the Frequency-Dependent Ultrasonic Attenuation," IEEE Transactions on Biomedical Engineering, vol. BME-30, No. 6, pp. 320-326, Jun. 1983 (Year: 1983).*

K. J. Parker et al., "Measurement of Ultrasonic Attenuation Within Regions Selected from B-Scan Images," IEEE Transactions on Biomedical Engineering, vol. BME-30, No. 8, pp. 431-437, Aug. 1983 (Year: 1983).*
H. Kim et al., "Estimation of Ultrasound Attenuation from Broadband Echo-Signals Using Bandpass Filtering," IEEE Transactions on Ultrasonics, Ferroelectrics, and Frequency Control, vol. 55, No. 5, pp. 1153-1159, May 2008 (Year: 2008).*
Y. Labyed et al., "A theoretical comparison of attenuation measurement techniques from backscattered ultrasound echoes," Journal of the Acoustic Society of America, vol. 129, No. 4, pp. 2316-2324, Apr. 2011 (Year: 2011).*
Hasan et al., "Using Nearest Neighbors for Accurate Estimation of Ultrasonic Attenuation in the Spectral Domain," IEEE Transactions on Ultrasonics, Ferroelectrics, and Frequency Control, vol. 60, No. 6, pp. 1098-1114, Jun. 2013 (Year: 2013).*
Y. Kanayama et al., "Real-Time Ultrasound Attenuation Imaging of Diffuse Fatty Liver Disease", Ultrasound in Medicine and Biology, vol. 39, No. 4, pp. 692-705, Apr. 2013 (Year: 2013).*
Duck F.A., "Chapter 4—Acoustic Properties of Tissue at Ultrasonic Frequencies," in Physical Properties of Tissues, London: Academic Press, 1990, pp. 73-135.
Golub G. et al., "The Differentiation of Pseudo-Inverses and Nonlinear Least Squares Problems Whose Variables Separate," SIAM Journal on Numerical Analysis, vol. 10, No. 2, pp. 413-432, Apr. 1, 1973 1973.
International Searching Authority, International Search Report and Written Opinion for application PCT/US2018/038951, mailed on Sep. 5, 2018.
Kim H. et al., "Hybrid Spectral Domain Method for Attenuation Slope Estimation," Ultrasound in Medicine and Biology, vol. 34, No. 11, pp. 1808-1819, Nov. 2008.
Kuc R. et al., "Reduced order Autoregressive Modeling for Centerfrequency Estimation," Ultrasonic Imaging, vol. 7, No. 3, pp. 244-251, Jul. 1985.
Labyed, Y, et al. "A theoretical comparison of attenuation measurement techniques from backscattered ultrasound echoes." The Journal of the Acoustical Society of America 129.4 (2011): 2316-2324.
Labyed, Y. et al. "Estimating the total ultrasound attenuation along the propagation path by using a reference phantom." The Journal of the Acoustical Society of America 128.5 (2010): 3232-3238.
Lin, T. et al., "Correlation of Ultrasonic-Attenuation with Pathologic Fat and Fibrosis in Liver-disease," Ultrasonic Imaging, vol. 10, No. 1, pp. 59-59, Jan. 1988.
Lu, Z.F. et al., "Ultrasound backscatter and attenuation in human liver with diffuse disease," Ultrasound in Medicine and Biology, vol. 25, No. 7, pp. 1047-1054, Sep. 1999.
Nam, K. et al., "Simultaneous Backscatter and Attenuation Estimation using a Least Squares Method with Constraints," Ultrasound in Medicine and Biology, vol. 37, No. 12, pp. 2096-2104, Dec. 2011.
Oelze M.L. et al, "Review of Quantitative Ultrasound: Envelope Statistics and Backscatter Coefficient Imaging and Contributions to Diagnostic Ultrasound," IEEE Transactions on Ultrasonics Ferroelectrics and Frequency Control, vol. 63, No. 2, pp. 336-351, Feb. 2016.
Sasso M. et al., "Controlled Attenuation Parameter (CAP): A Novel VCTE (TM) Guided Ultrasonic Attenuation Measurement for the Evaluation of Hepatic Steatosis: Preliminary Study and Validation in a Cohort of Patients with Chronic Liver Disease from Various Causes," Ultrasound in Medicine and Biology, vol. 36, No. 11, pp. 1825-1835, Nov. 2010.
Taylor KJW et al., "Quantitative US Attenuation in Normal Liver and in Patients with Diffuse Liver-Disease—Importance of Fat," Radiology, vol. 160, No. 1, pp. 65-71, Jul. 1986.
Yao, L.X. et al., "Backscatter Coefficient Measurements Using a Reference Phantom to Extract Depth-Dependent Instrumentation Factors," Ultrasonic Imaging, vol. 12, No. 1, pp. 58-70, Jan. 1, 1990 1990.

* cited by examiner

METHODS FOR ULTRASOUND SYSTEM INDEPENDENT ATTENUATION COEFFICIENT ESTIMATION

CROSS-REFERENCE TO RELATED APPLICATIONS

This application is a 371 U.S. National Phase application of PCT/US2018/038951, filed Jun. 22, 2018, which claims the benefit of U.S. Provisional Patent Application Ser. No. 62/524,043, filed on Jun. 23, 2017, and entitled "METHODS FOR ULTRASOUND SYSTEM INDEPENDENT ATTENUATION COEFFICIENT ESTIMATION," each of which is herein incorporated by reference in its entirety.

BACKGROUND

Ultrasound attenuation coefficient estimation ("ACE") is useful for clinical application. For example, estimates of ultrasound attenuation coefficient can be used to differentiate tumors and quantify fat content in liver.

In the example of fat content detection, the fat in liver affects the ultrasound propagation and is associated with the attenuation coefficient. As a result, the attenuation coefficient can be used as a liver fat assessment factor. Comparing to the gold standard, liver biopsy, ACE offers non-invasive and repeatable procedures.

The two most commonly used ACE methods include the spectral shift method and the reference phantom method. The spectral shift method estimates the center frequency downshift along depth; however, this method ignores beamforming and diffraction effects, which limits the estimation accuracy. On the other hand, in the reference phantom method, a well-calibrated phantom is used to normalize all of the ultrasound system dependent effects, such as focusing, time-gain compensation ("TGC"), and diffraction. However, in practice, a well-calibrated phantom is not always available and their ultrasound properties may change over time as the materials in the phantom degrade or otherwise change with time.

Thus, there remains a need for a method of estimating attenuation coefficient values that does not require a reference phantom for normalization while still being independent of ultrasound system effects.

SUMMARY OF THE DISCLOSURE

The present disclosure addresses the aforementioned drawbacks by providing a method for estimating an acoustic property of a physical medium in a region-of-interest using an ultrasound system. Ultrasound data are acquired from a plurality of depth locations along an ultrasound beam path within the region-of-interest. The ultrasound data includes at least first ultrasound data acquired in response to transmitting ultrasound to the region-of-interest at a first frequency and second ultrasound data acquired in response to transmitting ultrasound to the region-of-interest at a second frequency that is different from the first frequency. Frequency spectra ratio values are computed by computing a ratio between the first ultrasound data and the second ultrasound data acquired at each of the plurality of different depth locations, and an acoustic property value of the physical medium in the region-of-interest is computed from the plurality of frequency spectra ratio values. A report is generated based on the estimated acoustic property value of the physical medium.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for estimating acoustic properties in a region-of-interest in a subject or other object being imaged using a reference frequency method ("RFM") in which ultrasound data acquired at a given frequency are normalized by ultrasound data acquired at adjacent frequencies in order to provide estimations of the acoustic properties (e.g., attenuation coefficient, a backscatter coefficient, or both) that are independent of the ultrasound system used to acquire the underlying data. For instance, the amplitude of each frequency component can be normalized by a different frequency in the power spectrum to cancel out the system-dependent effects. Because the methods described in the present disclosure are system independent, they can be applied to any transducer geometry (e.g., linear or curved arrays) and using any beam pattern (e.g., focused or unfocused).

In ultrasound imaging, the power spectrum of backscattered RF signals can be modeled as, $$S(f_i, z_k) = G(f_i) \cdot TGC(z_k) \cdot D(f_i, z_k) \cdot BSC(f_i) \cdot A(f_i, z_k) \quad (1);$$

where $G(f_i)$ accounts for the transmit and receive transducer responses at the frequency $f_i$, where i is the frequency component index); $TGC(z_k)$ is the time-gain compensation ("TGC"), varying as a function of depth, $z_k$, where k is the depth index); $D(f_i, z_k)$ is the combined effects of focusing, beamforming, and diffraction; $BSC(f_i)$ is the backscatter coefficient which is assumed be to uniform in the region-of-interest ("ROI"); and $A(f_i, z_k)$ is the frequency dependent attenuation, which can be expressed as, $$A(f_i, z_k) = e^{-4 a f_i z_k} \quad (2);$$

where a is the attenuation coefficient. In many instances, it can be assumed that $A(f_i, z_k)$ is uniform in the ROI and that it is has a linear frequency dependency. The shape of the ROI is flexible, and in some instances may be a rectangle, a square, a sector, and so on. This type of model can be generally applicable to all ultrasound systems regardless of the beam pattern (e.g., unfocused or focused).

To estimate attenuation coefficient, a, certain multiplicative terms as in Eqn. (1) can be canceled first. It is a teaching of the methods described in the present disclosure that this can be accomplished by regarding an adjacent frequency, $f_{i-1}$, as a reference frequency and calculating the ratio between $S(f_i, z_k)$ and $S(f_{i-1}, z_k)$ as, $$Rs(f_i, z_k) = \frac{S(f_i, z_k)}{S(f_{i-1}, z_k)} = \frac{G(f_i) \cdot TGC(z_k) \cdot D(f_i, z_k) \cdot BSC(f_i) \cdot A(f_i, z_k)}{G(f_{i-1}) \cdot TGC(z_k) \cdot D(f_{i-1}, z_k) \cdot BSC(f_{i-1}) \cdot A(f_{i-1}, z_k)}. \quad (3)$$

The adjacent frequency, $f_{i-1}$, in Eqn. (3) is only one non-limiting example. More generally, the adjacent frequency can be $f_{i \pm n}$, where i and n are frequency indices that index the frequencies in a given range of frequencies. While i and n are integers (e.g., $i \geq 0$ and $n \geq 1$), the values of the frequencies, $f_{i \pm n}$, need not be integers, but instead can be any real-valued frequency. For instance, in one example $f_i$ can equal 5 MHz and $f_{i \pm n}$ can equal 5.1 MHz. In another example, $f_i$ can equal 5 MHz and $f_{i \pm n}$ can equal 6 MHz. It will thus be appreciated that the methods described in the present disclosure can be generalized to computing a ratio between signals acquired in response to a first transmit frequency and signals acquired in response to a second transmit frequency that is different from the first transmit frequency. Thus, while the adjacent frequency is referred to as $f_{i-1}$ in the present disclosure for the sake of providing an example, it will be appreciated that frequencies other than $f_{i-1}$ can be used as the adjacent frequency regarded as a reference frequency.

It can be generally assumed that the difference of beamforming and diffraction effects between $f_i$ and $f_{i-1}$ at the same depth can be ignored, such that, $$D(f_i, z_k) = D(f_{i-1}, z_k) \quad (4).$$

In addition, $TGC(z_k)$ is independent of frequency, $f_i$. Hence, these two terms can be cancelled after taking the ratio as in Eqn. (3), which results in, $$Rs(f_i, z_k) = \frac{G(f_i) \cdot BSC(f_i) \cdot A(f_i, z_k)}{G(f_{i-1}) \cdot BSC(f_{i-1}) \cdot A(f_{i-1}, z_k)}. \quad (5)$$

After taking the natural logarithm of both sides of Eqn. (5), the following linear relationship can be obtained, $$\ln(Rs(f_i, z_k)) = \ln(G(f_i)) - \ln(G(f_{i-1})) + \ln(BSC(f_i)) - \ln(BSC(f_{i-1})) - 4a(f_i - f_{i-1})z_k \quad (6).$$

The slope of $z_k$ ln $(Rs(f_i, Z_k))$ in Eqn. (6) with respect to the independent variable, $Z_k$, is, $$\text{slope} = -4a_i(f_i - f_{i-1}) \quad (1);$$

and thus, $$a_i = \frac{\text{slope}}{-4(f_i - f_{i-1})}; \quad (8)$$

where $a_i$ is the estimated attenuation coefficient at frequency component $f_i$. It should be appreciated that although natural logarithms are used above and in later portions of the present disclosure that other logarithms could also be implemented, such as a base-10 logarithm.

Figure 1A:
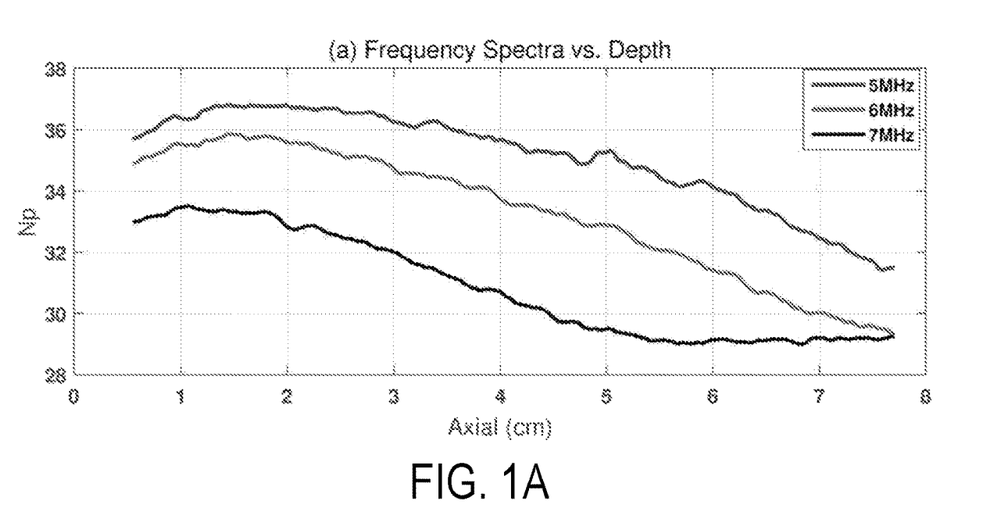
FIG. 1A. shows frequency power spectra after natural logarithm as a function of depth at three example frequency components, $f_i$, or 5, 6, and 7 MHz.
Figure 1B:
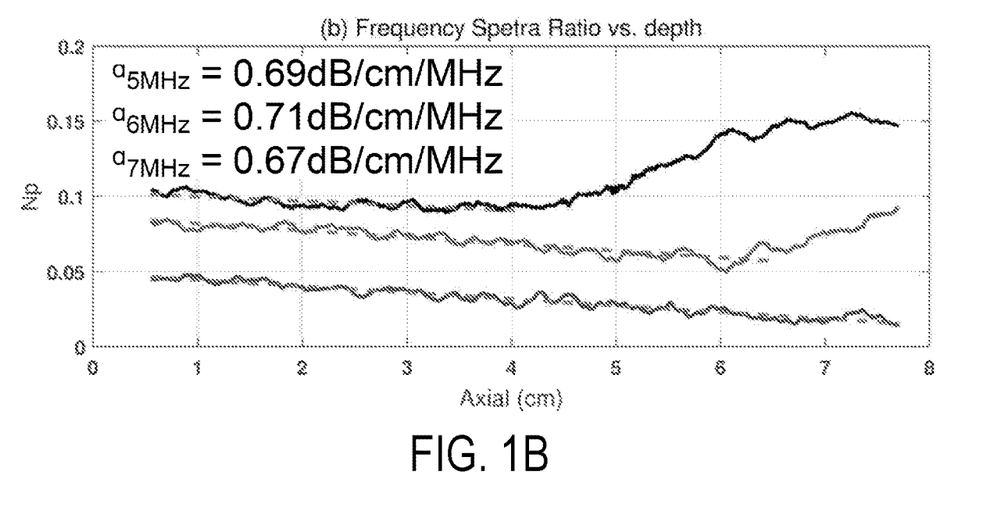
FIG. 1B. shows frequency spectra ratio after natural logarithm as a function of depth at the same frequency components. The frequency spectra ratio decay curves for 6 and 7 MHz were shifted upwards by 0.05 and 0.1, respectively, for better visualization.

FIG. 1A shows an example of a frequency power spectra after applying the natural logarithm (i.e., $\ln(S(f_i, z_k))$) as a function of depth at three example frequency components, $f_i$, of 5 MHz, 6 MHz, and 7 MHz. FIG. 1B shows the ratio of the spectra after applying the natural logarithm (i.e., $\ln(Rs(f_i, z_k))$) as a function of depth at the same frequency components. After taking the ratio, the frequency curves decay with similar slopes for different frequencies up to $z_k$ of 4 cm. However, the 6 MHz frequency curve starts to increase at round 6 cm depth and the 7 MHz frequency curve starts to increase at round 4 cm. This is because the higher frequency signals attenuate faster with depth compared to lower frequencies, and because electric noise starts to dominate (i.e., resulting in falsely elevated attenuation coefficient estimation) after certain depths. The linear fittings for each frequency are shown by the dashed lines with the attenuation coefficient values shown in the left upper corner of FIG. 1B. The values are converted to units of dB/cm/MHz.

The linearity versus depth for different frequency spectra ratio decay curves could be used as a quality control to determine the reliability of the attenuation estimation. For example, the residual error of linear fitting can be used as a metric to indicate reliability of attenuation estimation for a spectra ratio decay curve at a given frequency.

In another example of quality control, the maximum depth of valid linear fitting for a spectra ratio decay curve at a given frequency can be determined as the depth beyond which the curve no longer follows a linear decrease with depth. This information can then be used to determine the frequency components to be used for final attenuation estimation at a given depth. For instance, as one example the estimates at different frequencies can be averaged.

In another example of quality control, realistic boundaries for ultrasound attenuation can be selected based on ranges of attenuation expected for different soft tissues (e.g., based on reported ranges of values from literature), which can then be used to reject estimates that are unrealistic. For example, if the frequency spectra ratio presents a positive slope at a certain frequency, $f_i$, then the corresponding attenuation, $a_i$, would become a negative value, which is not realistic and thus should be eliminated from the final averaging process.

From plots such as the one shown in FIG. 1B, various attenuation coefficient values can be estimated at each frequency by combining all estimated slopes over the entire power spectrum. As one non-limiting example, the final attenuation coefficient a can be calculated by averaging all the estimations at different frequencies as, $$\bar{a} = \frac{\sum_{i=2}^{I} a_i}{I - 1}; \quad (9)$$

where I is the total number of frequency components to be used in the attenuation coefficient estimation. In the example of Eqn. (9), the attenuation coefficient, $a_i$, estimated at frequency component $f_i$ has the same weight during combination. A weighted averaging of attenuation coefficient values, $a_i$, can also be considered, such as by applying more weight to the center frequency and less weight to the frequencies that approach the bandwidth limit, or by applying more weight to estimates at frequencies with better linear fit (e.g., those with less fitting error) with depth.

In another non-limiting example, the spectra ratio decay curves at different frequencies can be first averaged. The average may be a weighted average, or a non-weighted average. Then, the slope of the of the averaged decay curve can be estimated along the depth to calculate the final attenuation coefficient.

In the expression of spectra ratio, $Rs(f_i, z_k)$ as in Eqn. (5), if the transducer response at each frequency, $G(f_i)$, can be calibrated in advance, then this term becomes a known parameter in the equation.

As one non-limiting example, the transducer response can be measured with a hydrophone under water. The power spectrum of the signals transmitted by the transducer and received by the hydrophone corresponds to the one-way (i.e., transmit) transducer response at different frequency components. This spectrum can then be squared to calculate the two-way transducer response by assuming the transducer receive response is the same as the one for transmit.

Another non-limiting example for calibrating the transducer response, $G(f_i)$, is that the transducer transmits to air directly, or transmits to a strong reflecting interface in water, and then receives the echoes. The power spectrum of the echoes received by the transducer itself accounts for both transmit and receive transducer responses.

With a calibrated transducer response, the frequency dependency of the backscatter coefficient, $BSC(f_i)$, in Eqn. (5) can be estimated simultaneously with the attenuation coefficient. The backscatter coefficient can be modelled as, $$BSC(f_i) = b f_i^{n_b} \quad (10);$$

where b is a constant coefficient and $n_b$ is the frequency dependency. Substituting (10) in Eqn. (5) yields, $$Rs(f_i, z_k) = R_G(f_i) \cdot \frac{b f_i^{n_b}}{b f_{i-1}^{n_b}} \cdot \frac{e^{-4 a f_i z_k}}{e^{-4 a f_{i-1} z_k}}; \quad (11)$$

where $R_G(f_i)$ is the transducer frequency response ratio, $G(f_i)/G(f_{i-1})$. Taking the natural logarithm on both sides of Eqn. (11) results in, $$\ln(Rs(f_i, z_k)) = \ln(R_G(f_i)) + n_b(f_i - f_{i-1}) - 4 a z_k (f_i - f_{i-1}) \quad (12).$$

A linear fit of $\ln(Rs(f_i, z_k))$ versus depth can then be performed, as shown in FIG. 1B, to find the intercept with the vertical axis: $y_{intercept}$. Then the frequency dependent backscatter coefficient can be estimated as, $$n_{b,i} = \frac{y_{intercept} - \ln(R_G(f_i))}{(f_i - f_{i-1})}; \quad (13)$$

where $n_{b,i}$ is the estimated backscatter coefficient at $f_i$. Afterwards, all of the $n_{b,i}$ values estimated over the power spectrum can be combined for a final estimation of the backscatter coefficient. One example of combination is weighted or unweighted averaging. In another example, the $n_{b,i}$ values can be plotted as a function of frequency, and as a first order approximation, the slope of $n_{b,i}$ versus frequency can be used as a parameter to characterize the tissue.

Because tissues can often have more complicated and non-uniform small structures that lead to larger oscillations in the frequency spectra ratio decay curves, in some instances, the frequency slope fitting method may have lower estimation accuracy. In these instances, a least squares method ("LSM") can be applied to improve the estimation accuracy. In LSM, the ratio of the spectra after natural logarithm (i.e., $\ln(Rs(f_i, z_k))$) can be fit to a one-parameter model or to a multiple-parameter model. The model can automatically search for the best solution to minimize the estimation errors. A two-parameter model and a one-parameter model are provided as two non-limiting examples.

In the two-parameter model, the transducer response at each frequency can be measured or calibrated in advance. Then following Eqn. (12), the following expression can be derived:

$$(f_i - f_{i-1}) \cdot (n_b - 4 a z_k) = \ln(Rs(f_i, z_k)) - \ln(R_G(f_i)) \quad (14).$$

Eqn. (14) can be simplified based on the following expressions, $$A(f_i, z_k)[(f_i - f_{i-1}) \quad -4(f_i - f_{i-1}) z_k]; \quad (15)$$

$$U = \begin{bmatrix} n_b \\ a \end{bmatrix}; \quad (16)$$

$$V(f_i, z_k) = [\ln(Rs(f_i, z_k)) - \ln(R_G(f_i))]; \quad (17)$$

where A is a matrix with a size of $N_{i,k} \times 2$, for $N_{i,k}$ total number of frequency components, $f_i$, and depths, $z_k$, used in the estimation; U is a column vector with two elements for the parameters, $n_b$, and a, to be estimated; and V is a column vector with a size of $N_{i,k} \times 1$.

Using the expressions in Eqns. (15)-(17), Eqn. (14) can be written as, $$AU = V \quad (18).$$

To solve the two unknowns, $n_b$ and a, in Eqn. (18), two or more measurements of $V(f_i, z_k)$ can be sufficient. As one example, the two measurements could be obtained by varying the frequency component at two different values (e.g., $f_i = f_1, f_2$), or by changing the measurement depth (e.g., $z_k$ $z_1$, $z_2$), or both. When using a broadband transducer with a large range of frequencies, or when the ROI has a relatively large range of depth (i.e., $N_{i,k} > 2$), multiple values of $n_b$ and a can be estimated. These $n_b$ and a values can be combined to generate a final estimation. For instance the combination can include a weighted averaging, and unweighted averaging, or other suitable combination.

Another way to narrow down the estimation to a single solution is to apply a least squares method, such as, $$[\hat{n}_b, \hat{a}] = \arg\min_{n_b, a} \sum_{k=1}^{K} \sum_{i=1}^{I} \{\ln(Rs(f_i, z_k)) - \ln(R_G(f_i)) - (f_i - f_{i-1}) \cdot (n_b - 4 a z_k)\}^2; \quad (19)$$

where K and I are the total number of depths and frequency components used in the LSM fitting, respectively.

In the case of two measurements (i.e., $N_{i,k}=2$), the solution of Eqn. (19) will correspond to the direct inverse result in Eqn. (18) as, $$U=A^{-1}V \quad (20).$$

For more than two measurements (i.e., $N_{i,k}>2$), Eqn. (19) will correspond to the pseudo inverse results in Eqn. (18) as, $$U=[A^*A]^{-1}A^*V \quad (21);$$

where $A^*$ is the transpose, or conjugate transpose, of the matrix, A.

In this two-parameter model, the frequency dependency of the backscatter coefficient $n_b$, and the attenuation coefficient, a, can be estimated simultaneously.

If the transducer frequency response remains unknown, this term will need to be canceled in order to estimate the attenuation coefficient. In this case, a one-parameter model can be used. In the one-parameter model, the spectra ratio Rs $(f_i,z_k)$ can be first normalized by the value obtained at a reference depth, $z_r$ (i.e., $\ln(Rs(f_i, z_r))$, where r is the reference depth index). Afterwards, both the transducer frequency response and backscatter coefficient in Eqn. (5) can be canceled due to their being independent of depth. Multiple reference depths, $z_r$, can be used to average out errors caused by noise, such as electric noise. The normalization step can be described as, $$Rs_{nor}(f_i, z_k, z_r) = \frac{Rs(f_i, z_k)}{Rs(f_i, z_r)} \quad (22)$$
$$= \frac{A(f_i, z_k)}{A(f_i, z_r)} \cdot \frac{A(f_{i-1}, z_r)}{A(f_{i-1}, z_k)}.$$

Taking the natural logarithm of both sides of Eqn. (22) results in, $$\ln(Rs_{nor}(f_i, z_k, z_r)) = -4af_i z_k + 4af_i z_r - 4af_{i-1} z_r + \quad (23)$$
$$4af_{i-1} z_k$$
$$= -4a(f_i - f_{i-1})(z_k - z_r);$$

when $z_k \neq z_r$.

To simplify Eqn. (23), in this one-parameter model, the following expressions can be used:

$$V(f_i,z_k,z_r)=[\ln(Rs_{nor}(f_i,z_k,z_r))] \quad (24);$$

$$A(f_i,z_k,z_r)=[-4(f_i-f_{i-1})(z_k-z_r)] \quad (25);$$

$$U=a$$

In this one-parameter model, both V and A are two column vectors with size of $N_{i,k,r} \times 1$, where $N_{i,k,r}$ is the total number of $f_i$, $z_k$, and $z_r$ used in the estimation model, and U is a scalar with a single element equal to the attenuation coefficient, a. Then, Eqn. (24) can be written as, $$V=AU \quad (26).$$

There is only one unknown, a, to be solved in this one-parameter tissue model. One value of $V(f_i, z_k, z_r)$ value should generate one estimation of attenuation coefficient, a. If multiple measurements are available, multiple attenuation coefficient values can be estimated and can be combined to generate a final estimation of attenuation coefficient, such as by using a weighted or unweighted combination or averaging.

In some implementations, an LSM method can be applied to narrow down the estimation to a single solution, such as, $$[\hat{a}] = \arg\min_a \sum_{r=1}^{R}\sum_{k=1}^{K}\sum_{i=1}^{I} \{\ln(Rs_{nor}(f_i, z_k, z_r)) + 4a(f_i - f_{i-1})(z_k - z_r)\}^2; \quad (27)$$

when $z_k \neq z_r$, and where R is the total number of reference depths used in the least squares fitting. In the case of one measurement (i.e., $N_{i,k,r}=1$), the solution of Eqn. (27) will correspond to the direct inverse result in Eqn. (26), $$U=A^{-1}V \quad (28).$$

For more than one measurement (i.e., $N_{i,k,r}>1$), Eqn. (27) will correspond to the pseudo inverse result in Eqn. (26) as, $$U=[A^*A]^{-1}A^*V \quad (29).$$

To stabilize the estimation in LSM, the models can be subjected to certain constraints as, $$a_{min} \leq a \leq a_{max} \quad (30).$$

$$n_{b,min} \leq n_b \leq n_{b,max}$$

Realistic boundaries can be selected for a and $n_b$ based on the physical properties of different physical media, such as soft tissues. For example, a relatively safe range of liver attenuation coefficient constraints can be selected as, $$0 \leq a_{liver}(\text{dB/cm/MHz}) \leq 2 \quad (31).$$

The maximum and minimum constraints can also be adaptively determined based on the acquired data. For instance, when using the one-parameter model, because one value of $V(f_i, z_k, z_r)$ can generate one attenuation coefficient value, a, all possible attenuation coefficient values can first be calculated using all measurements as, $$a = \frac{\ln(Rs_{nor}(f_i, z_k, z_r))}{-4(f_i - f_{i-1})(z_k - z_r)}; \quad (32)$$

or, $$U=V./A \quad (33);$$

where "./" stands for an element-wise division. As a non-limiting example, the distribution of attenuation coefficient values can be obtained by the histogram of all attenuation coefficient values.

Figure 2:
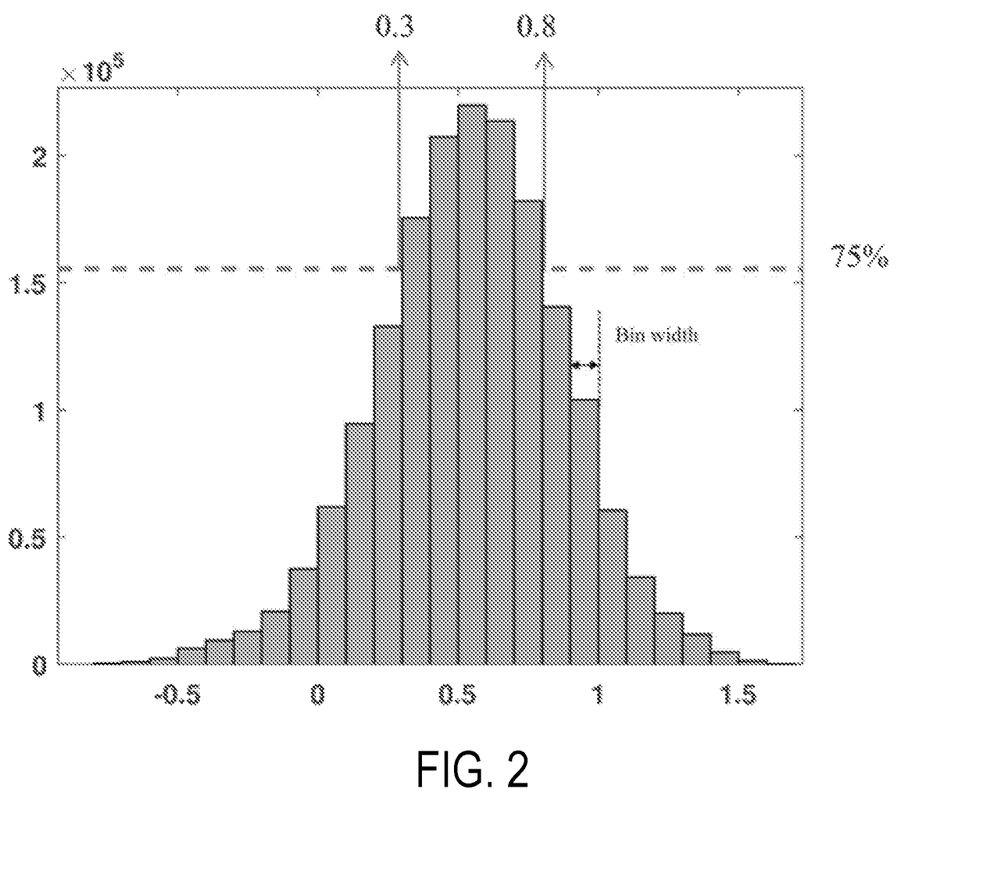
FIG. 2. shows a histogram of possible attenuation coefficients. The data were acquired from a commercial phantom with nominal value of 0.5 dB/cm/MHz. The phantom was imaged with unfocused plane wave imaging at 5 MHz center frequency.

FIG. 2 shows a histogram example obtained from a 0.5 dB/cm/MHz phantom. In this example, the bin width of the histogram is set as 0.1 dB/cm/MHz. The cutoff boundaries are selected at 75 percent of the maximum value (indicated by red dashed lines) on both sides. In FIG. 2, $a_{min}=0.3$ dB/cm/MHz and $a_{max}=0.8$ dB/cm/MHz. Then, these values can be used as constraints for a search range in the one-parameter model LSM.

In practice, the bin width and cut-off boundaries can be adjusted flexibly to accommodate different conditions. Different cut-off determination methods can also be applied such as applying curve fittings to the histogram. As a non-limiting example, a Gaussian function can be fitted to the histogram in FIG. 2. The position of the peak of the fitted Gaussian function can be regarded as the best estimated value of attenuation coefficient (thereby providing another method for estimating the attenuation coefficient), and the lower and upper limit of attenuation coefficient for an LSM search can be determined from the fitted Gaussian function (for example, when the Gaussian function drop to 75 percent of its peak value).

The two-parameter model constraints can be determined in a similar manner.

As one non-limiting example, for quality control the residual errors of the one-parameter or two-parameter least squares models can be used as a metric to indicate reliability of the attenuation estimation.

Clinically, during ultrasound scanning, the body wall usually induces reverberation artifacts to the soft tissues below. In the presence of these reverberation artifacts, it may be challenging for accurate attenuation coefficient estimation. In these instances, the methods described in the present disclosure can be combined with harmonic imaging to reduce the reverberation artifacts. For example, B-mode images can be acquired using a harmonic imaging mode with specially designed pulses (e.g., pulse inversion, amplitude modulation, pulse inversion amplitude modulation, or other suitable methods) or using filter based harmonic imaging. After pulse recombination, the methods described in the present disclosure can be applied to estimate attenuation coefficient, backscatter coefficient, or both.

Clutter filters can also be used with multiple frame acquisitions to suppress reverberation artifacts. As a non-limiting example, clutter filters based on singular value decomposition as described in co-pending patent applications (PCT/US2017/016190, U.S. patent application Ser. No. 15/887,029, which are herein incorporated by reference in their entirety) can be used to reject undesired signals. The reverberations from the body wall will generally have different motion patterns (e.g., less motion compared to the real tissue motion due to breathing). The sonographer can also indicate small motion when imaging the targets, such as by translating the transducer slightly. The reverberations from the body wall will have more stationary motion patterns because of a more fixed location relative to the transducer surface, as compared to the tissues underneath. In both examples, the reverberations can be identified and rejected by the clutter filter.

For a more general model, tissue attenuation can be written as, $$A(f_i, z_k) = e^{-4af_i^{n_a} z_k}; \tag{34}$$

where $n_a$ is the attenuation frequency dependency. The examples described above assume $n_a=1$; however, the methods can also be readily adapted for the nonlinear case where $n_a \neq 1$. For example, in the frequency slope fitting method, Eqn. (8) can be modified as, $$a_i = \frac{\text{slope}}{-4(f_i^{n_a} - f_{i-1}^{n_a})}. \tag{35}$$

No closed form solution exists for solving Eqn. (35). As one non-limiting example, a variable projection ("VARPRO") method can be used to estimate attenuation coefficient. For the example of the one-parameter LSM model, Eqn. (34) can be substituted in Eqn. (22) to yield, $$Rs_{nor}(f_i, z_k, z_r) = \frac{A(f_i, z_k)}{A(f_i, z_r)} \cdot \frac{A(f_{i-1}, z_r)}{A(f_{i-1}, z_k)} \tag{36}$$

$$= \frac{e^{-4af_i^{n_a} z_k} \cdot e^{-4af_{i-1}^{n_a} z_r}}{e^{-4af_i^{n_a} z_r} \cdot e^{-4af_{i-1}^{n_a} z_k}}.$$

Taking the natural logarithm on both sides of Eqn. (36) results in, $$\ln(Rs_{nor}(f_i, z_k, z_r)) = -4af_i^{n_a} z_k + 4af_i^{n_a} z_r - 4af_{i-1}^{n_a} z_r + \tag{37}$$
$$4af_{i-1}^{n_a} z_k$$
$$= -4a(f_i^{n_a} - f_{i-1}^{n_a})(z_k - z_r).$$

In the one-parameter nonlinear case, this results in, $$AU=V \tag{38};$$

where, $$V(f_i, z_k, z_r) = \ln(Rs_{nor}(f_i, z_k, z_r)) \tag{39};$$

$$A(f_i, z_k, z_r, n_a) = -4(f_i^{n_a} - f_{i-1}^{n_a})(z_k - z_r)$$

$$U=a$$

As both U and $n_a$ are unknown in Eqn. (38), their joint estimation corresponds to a nonlinear least squares estimation. However, because of the separable structure of Eqn. (38), these unknown parameters can be sequentially determined using a VARPRO technique.

In such an implementation, for a given $n_a$, U is first analytically determined as a function of $n_a$ using an ordinary (e.g., linear) least squares, $$[\hat{a}] = \arg \min_a \sum_{r=1}^{R} \sum_{k=1}^{K} \sum_{i=1}^{I} \{\ln(Rs_{nor}(f_i, z_k, z_r)) + 4a(f_i^{n_a} - f_{i-1}^{n_a})(z_k - z_r)\}^2; \tag{40}$$

or $$U(n_a) = (A^*(n_a)A(n_a))^{-1}A(n_a)V \tag{41}.$$

Eqn. (41) corresponds to the pseudo inverse result (i.e., more than one measurement) in Eqn. (40), as one non-limiting example.

The resulting expression of $U(n_a)$ is then embedded into the nonlinear least squares residual, $J(n_a)$, to yield, $$J(n_a) = \|A(n_a)U(n_a) - V\|_2^2 \tag{42}$$
$$= \|A(n_a)(A^*(n_a)A(n_a))^{-1}A^*(n_a)V - V\|_2^2.$$

Then, $n_a$ can move at a small step size, Ana, to yield an updated value as, $$n_a' = n_a + \Delta n_a \qquad \#.$$

The updated value, $n_a'$, will be repeatedly updated as described above until it covers the entire predefined search range, $n_{a,min} \leq n_a \leq n_{a,max}$. A realistic search range can be selected for $n_a$ based on known properties of soft tissues, such as $1 \leq n_a \leq 2$. For non-limiting examples, $n_a$ can move from the minimum limit to the maximum limit, or along the opposite direction.

After the linear search of $n_a$ within the predefined search range, the minimizing value of $n_a$ can be identified when the residue $J(n_a)$ gets to minimum. Once an optimal value of $n_a$ has been identified, the corresponding attenuation coefficient, a, estimated with that $n_a$ value can be selected as the final estimation. For the two-parameter LSM model, $n_a$ can be similarly determined via VARPRO and then utilized within the derivation of optimal estimations of $n_b$ and a, $$[n_b, a] = \underset{n_b, a}{\arg\min} \sum_{k=1}^{K} \sum_{i=1}^{I} \{\ln(Rs(f_i, z_k)) - \ln(R_G(f_i)) - (f_i^{n_a} - f_{i-1}^{n_a}) \cdot (n_b - 4az_k)\}^2. \quad (43)$$

Figure 3:
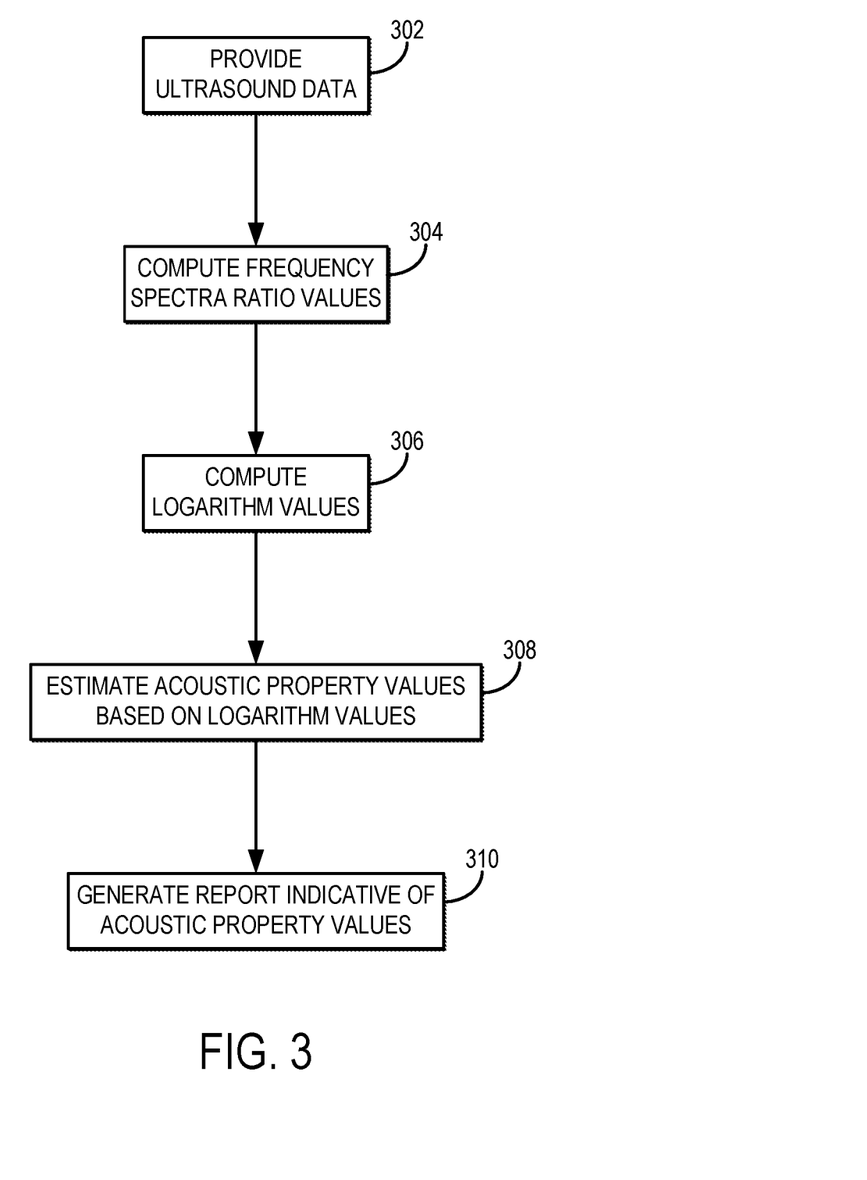
FIG. 3 is a flowchart setting forth the steps of an example method for estimating acoustic properties of a physical medium, such as a tissue, from ultrasound data using a reference frequency method.

Referring now to FIG. 3, a flowchart is illustrated as setting forth the steps of an example method for estimating acoustic property values of a physical medium using a reference frequency method. The physical medium can be a tissue, such as soft tissues in a subject, and the acoustic property values can be attenuation coefficient values, backscatter coefficient values, or both.

The method includes providing ultrasound data to a computer system for processing, as indicated at step 302. Providing the ultrasound data can include retrieving previously acquired data from a memory or other data storage, or can include acquiring data with an ultrasound system and communicating that data to a computer system, which may form a part of the ultrasound system.

In general, the ultrasound data include first ultrasound data acquired at a first frequency and second ultrasound data acquired at a second frequency that is spectrally adjacent the first frequency, as described above. Both the first and second ultrasound data are acquired over a plurality of different depth locations in a region-of-interest containing at least one physical medium for which acoustic property values will be estimated. The ultrasound data can be acquired over a range of different frequency values, such as a plurality of different first and second frequency values.

Frequency spectra ratio values are computed using the first and second ultrasound data, as indicated at step 304. For instance, a frequency spectra ratio value can be computed as the ratio between first ultrasound data and second ultrasound data acquired from the same depth location. The logarithm of each frequency spectra ratio value is computed to generate logarithm values, as indicated at step 306, and the acoustic property values are computed based at least in part on the logarithm values, as indicated at step 308. As described above, the logarithm values can be natural logarithm values; however, it should be noted that logarithms other than the natural logarithm can be used in the methods described in the present disclosure. For instance, a base-10 logarithm can be used to replace the natural logarithm in the methods described above to estimate attenuation coefficient and backscatter coefficient in a similar manner.

In some implementations, the acoustic property values include attenuation coefficient values, and estimating the attenuation coefficient values includes forming a frequency spectra ratio decay curve by plotting the natural logarithm values as a function of depth. The slope of this curve can be computed and an attenuation coefficient value estimated based on the slope. The slope can be computed using a linear fitting or a nonlinear fitting. When a nonlinear fitting is used, a method such as a VARPRO method can be implemented.

Multiple such curves can be computed for frequency spectra ratio values computed based on ultrasound data acquired at different frequencies, and the attenuation coefficient values computed for these multiple different curves can be combined to generate a final estimate of the attenuation coefficient. The attenuation coefficient values can be combined, for instance, using an averaging, which may be a weighted averaging.

The y-intercept of such curves can be computed and a backscatter coefficient can be estimated based on the y-intercept value. In these implementations, a transducer response can also be provided to the computer system and used to weight the frequency spectra ratio values.

In some other implementations, estimating the acoustic property values includes fitting the natural logarithm values to a parametric model of the frequency spectra ratio. The parametric model can be a one-parameter model, in which case the acoustic property values can include attenuation coefficients. The parametric model can also be a two-parameter model, in which case the acoustic property values can include attenuation and backscatter coefficients. Other parametric models could also be implemented. Fitting the natural logarithm values to the parametric model can include using a least-squares estimation. The least-squares estimation can be constrained using one or more constraints, such as constraints on the expected acoustic property values for the physical medium, or adaptive data generated constraints.

The description provided above assumed that the transmitted ultrasound beams are perpendicular to the transducer surface. The methods described in the present disclosure may, however, be applied to steered ultrasound beams. In the steered beam case, the "normalization along depth" described above can be understood as a more general normalization along the ultrasound path. That is, depth and depth locations will be understood to mean a position along the ultrasound path.

As another example, acoustic properties of the same physical region can be estimated using ultrasound beams steered at different angles. These estimations can be combined (for example, using weighted or unweighted average) to provide a final estimation of the acoustic properties.

After the acoustic property values have been estimated, a report can be generated based on the acoustic property values, as indicated at step 310. As one example, the report can include a digital image that depicts a spatial distribution of the acoustic property values in the region-of-interest. As another example, the report can include data plots, textual information, or other forms of visually depicting or representing the acoustic property values.

Figure 4:
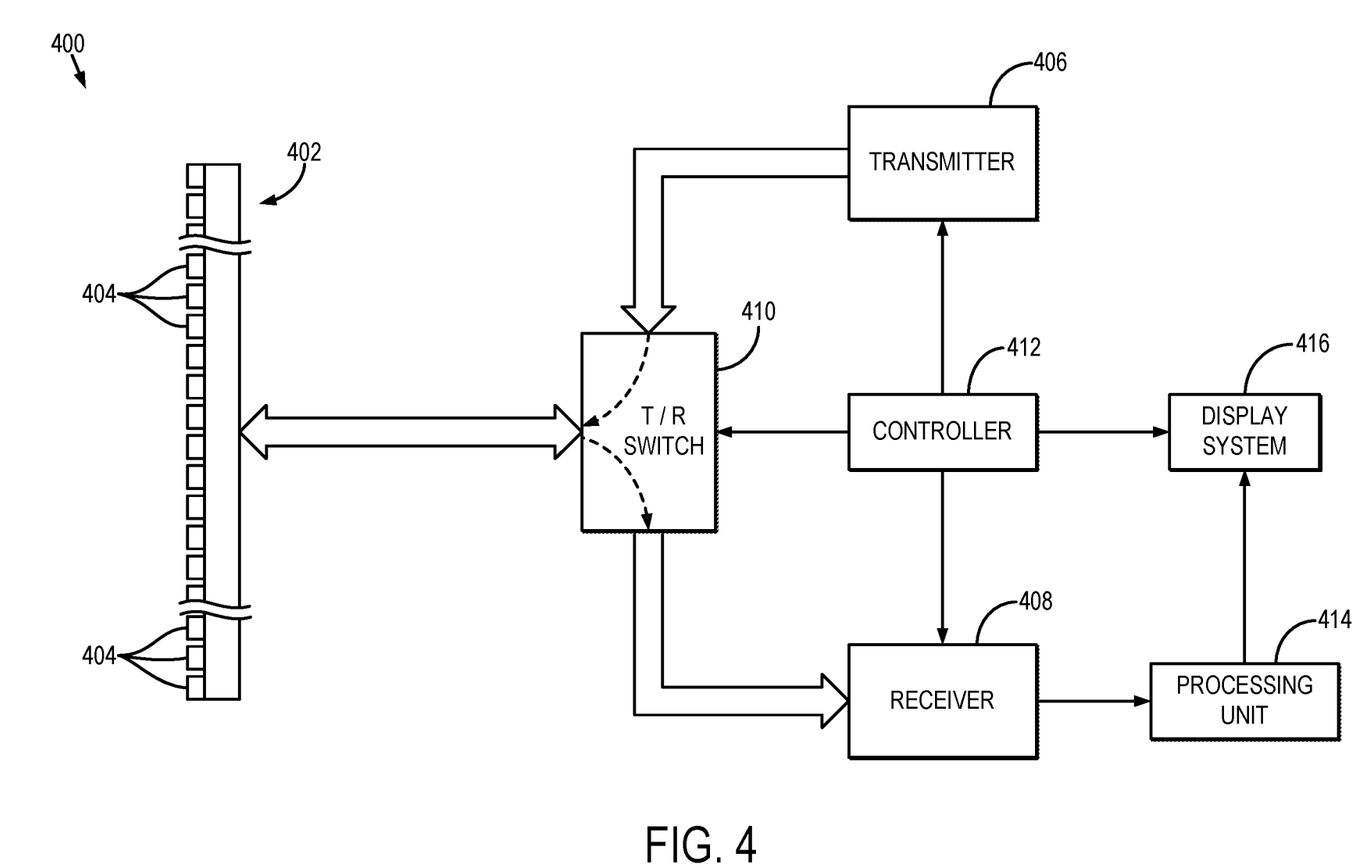
FIG. 4 is a block diagram of an example ultrasound system that can implement the methods described in the present disclosure.

FIG. 4 illustrates an example of an ultrasound system 400 that can implement the methods described in the present disclosure. The ultrasound system 400 includes a transducer array 402 that includes a plurality of separately driven transducer elements 404. The transducer array 402 can include any suitable ultrasound transducer array, including linear arrays, curved arrays, phased arrays, and so on. Similarly, the transducer array 402 can include a 1D transducer, a 1.5D transducer, a 1.75D transducer, a 2D transducer, a 3D transducer, and so on.

When energized by a transmitter 406, a given transducer element 404 produces a burst of ultrasonic energy. The ultrasonic energy reflected back to the transducer array 402 (e.g., an echo) from the object or subject under study is converted to an electrical signal (e.g., an echo signal) by each transducer element 404 and can be applied separately to a receiver 408 through a set of switches 410. The transmitter 406, receiver 408, and switches 410 are operated under the control of a controller 412, which may include one or more processors. As one example, the controller 412 can include a computer system.

The transmitter 406 can be programmed to transmit unfocused or focused ultrasound waves. In some configurations, the transmitter 406 can also be programmed to transmit diverged waves, spherical waves, cylindrical waves, plane waves, or combinations thereof. Furthermore, the transmitter 406 can be programmed to transmit spatially or temporally encoded pulses.

The receiver 408 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 406 and the receiver 408 can be programmed to implement a high frame rate. For instance, a frame rate associated with an acquisition pulse repetition frequency ("PRF") of at least 100 Hz can be implemented. In some configurations, the ultrasound system 400 can sample and store at least one hundred ensembles of echo signals in the temporal direction.

The controller 412 can be programmed to design an imaging sequence as known in the art. In some embodiments, the controller 412 receives user inputs defining various factors used in the design of the imaging sequence.

A scan can be performed by setting the switches 410 to their transmit position, thereby directing the transmitter 406 to be turned on momentarily to energize transducer elements 404 during a single transmission event according to the imaging sequence. The switches 410 can then be set to their receive position and the subsequent echo signals produced by the transducer elements 404 in response to one or more detected echoes are measured and applied to the receiver 408. The separate echo signals from the transducer elements 404 can be combined in the receiver 408 to produce a single echo signal.

The echo signals are communicated to a processing unit 414, which may be implemented by a hardware processor and memory, to process echo signals or images generated from echo signals. As an example, the processing unit 414 can estimate acoustic properties of a physical medium, such as a soft tissue, using the methods described in the present disclosure. Images produced from the echo signals by the processing unit 414 can be displayed on a display system 416.

Figure 5:
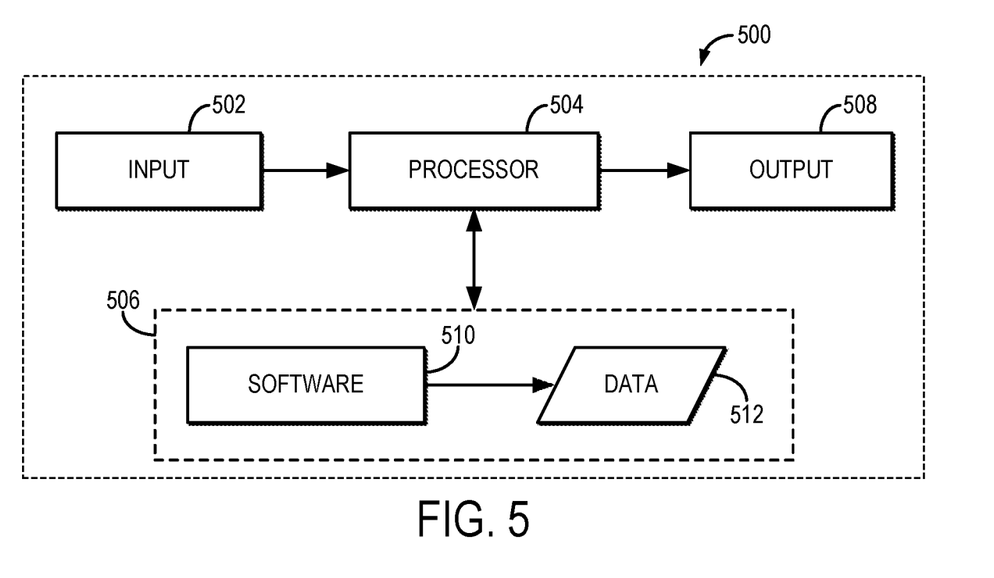
FIG. 5 is a block diagram of an example computer system that can implement the methods described in the present disclosure.

Referring now to FIG. 5, a block diagram of an example of a computer system 500 that can perform the methods described in the present disclosure is shown. The computer system 500 generally includes an input 502, at least one hardware processor 504, a memory 506, and an output 508. Thus, the computer system 500 is generally implemented with a hardware processor 504 and a memory 506. The computer system 500 may also be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 500 may operate autonomously or semi-autonomously, or may read executable software instructions from the memory 506 or a computer-readable medium (e.g., a hard drive, a CD-ROM, flash memory), or may receive instructions via the input 502 from a user, or any another source logically connected to a computer or device, such as another networked computer or server. Thus, in some embodiments, the computer system 500 can also include any suitable device for reading computer-readable storage media.

In general, the computer system 500 is programmed or otherwise configured to implement the methods and algorithms described in the present disclosure. For instance, the computer system 500 can be programmed to estimate acoustic properties of a physical medium, such as a soft tissue, using the method described in the present disclosure.

The input 502 may take any suitable shape or form, as desired, for operation of the computer system 500, including the ability for selecting, entering, or otherwise specifying parameters consistent with performing tasks, processing data, or operating the computer system 500. In some aspects, the input 502 may be configured to receive data, such as data acquired with an ultrasound system. Such data may be processed as described above to estimate acoustic properties, such as attenuation coefficient, backscatter coefficient, or both, or a physical medium, such as a soft tissue. In addition, the input 502 may also be configured to receive any other data or information considered useful for estimating acoustic properties of a physical medium, such as a soft tissue, using the methods described above. For instance, the input 502 may also be configured to receive transducer response data or reference depth data, as described above.

Among the processing tasks for operating the computer system 500, the one or more hardware processors 504 may also be configured to carry out any number of post-processing steps on data received by way of the input 502.

The memory 506 may contain software 510 and data 512, such as data acquired with an ultrasound system, and may be configured for storage and retrieval of processed information, instructions, and data to be processed by the one or more hardware processors 504. In some aspects, the software 510 may contain instructions directed to estimate acoustic properties of a physical medium, such as a soft tissue, from ultrasound data.

In addition, the output 508 may take any shape or form, as desired, and may be configured for displaying images, maps, data plots, textual information, or other visual depictions or representations of acoustic properties, in addition to other desired information.

The present disclosure has described one or more preferred embodiments, and it should be appreciated that many equivalents, alternatives, variations, and modifications, aside from those expressly stated, are possible and within the scope of the invention.

The invention claimed is:

1. A method for estimating an acoustic property of a physical medium in a region-of-interest using an ultrasound system, the steps of the method comprising:
   (a) transmitting ultrasound to the region-of-interest using a transducer of the ultrasound system, wherein the ultrasound is transmitted in a single transmission event with a bandwidth comprising a single center frequency, wherein the bandwidth contains a first frequency and a second frequency that is different from the first frequency, wherein the ultrasound is transmitted at each frequency in the bandwidth using a same aperture of the transducer;
   (b) acquiring ultrasound data from a plurality of depth locations along an ultrasound beam path within the region-of-interest using the transducer of the ultrasound system, the ultrasound data comprising at least first ultrasound data acquired in response to the ultrasound transmitted to the region-of-interest at the first frequency and second ultrasound data acquired in response to the ultrasound transmitted to the region-of-interest at the second frequency, wherein the first ultrasound data comprise a first power spectrum of backscattered radio frequency (RF) signals and the second ultrasound data comprise a second power spectrum of backscattered RF signals;

(c) computing a plurality of frequency spectra ratio values by computing a ratio between the first power spectrum in the first ultrasound data and the second power spectrum in the second ultrasound data acquired at each of the plurality of different depth locations;

(d) estimating an acoustic property value of a physical medium in the region-of-interest from the plurality of frequency spectra ratio values; and (e) generating a report based on the estimated acoustic property value of the physical medium.

2. The method as recited in claim 1, wherein the acoustic property value is an attenuation coefficient.

3. The method as recited in claim 2, wherein estimating the attenuation coefficient includes computing logarithm values by computing a logarithm of the frequency spectra ratio values, forming a frequency spectra ratio decay curve by arranging the logarithm values as a function of depth location, computing a slope over a portion of the frequency spectra ratio decay curve, and estimating the attenuation coefficient based on the slope.

4. The method as recited in claim 3, wherein the slope is computed based on a linear fitting.

5. The method as recited in claim 4, wherein a reliability of the attenuation coefficient is estimated based on a residual error of the linear fitting.

6. The method as recited in claim 4, wherein the portion of the frequency spectra ratio decay curve is selected as a range of depth locations over which the frequency spectra ratio decay curve follows a linear decrease as a function of depth location at the first frequency.

7. The method as recited in claim 3, wherein the slope is computed based on a nonlinear fitting.

8. The method as recited in claim 7, wherein the nonlinear fitting is computed based in part on a variable projection (VARPRO) method.

9. The method as recited in claim 2, wherein estimating the attenuation coefficient includes computing logarithm values as a logarithm of the plurality of frequency spectra ratio values and fitting the logarithm values to a parametric model to estimate the attenuation coefficient.

10. The method as recited in claim 9, wherein the parametric model is a one-parameter model of frequency spectra ratio and estimating the attenuation coefficient includes normalizing the plurality of frequency spectra ratio values by reference depth data before computing the logarithm values.

11. The method as recited in claim 10, wherein the reference depth data are ultrasound data acquired at the first frequency at one or more reference depths.

12. The method as recited in claim 9, wherein the parametric model is a two-parameter model of frequency spectra, and estimating the attenuation coefficient also includes estimating a backscatter coefficient.

13. The method as recited in claim 12, wherein step (b) is repeated using at least one of different first and second frequency values or different depth locations in each transmission event, such that the plurality of frequency spectra ratios correspond to at least one of multiple frequency measurements or multiple depth measurements.

14. The method as recited in claim 9, wherein fitting the logarithm values to the parametric model includes using a least-squares estimation.

15. The method as recited in claim 9, wherein fitting the logarithm values to the parametric model includes constraining the fitting using a constraint.

16. The method as recited in claim 15, wherein the constraint is a physical medium constraint that defines an expected range of attenuation coefficient values for the physical medium.

17. The method as recited in claim 15, wherein the constraint is a data generated constraint that is an adaptively determined constraint based at least in part on the frequency spectra ratio values.

18. The method as recited in claim 1, wherein step (b) is repeated for a plurality of different first frequency and second frequency values in each transmission event, step (c) is repeated for each of the plurality of different first frequency and second frequency values, and step (d) includes estimating a different acoustic property value for each of the plurality of different first frequency values and estimating a final acoustic property value based on a combination of the different acoustic property values.

19. The method as recited in claim 18, wherein the combination of the different acoustic property values includes averaging the different acoustic property values.

20. The method as recited in claim 19, wherein the different acoustic property values are averaged using a weighted averaging.

21. The method as recited in claim 1, wherein the acoustic property value is a backscatter coefficient.

22. The method as recited in claim 21, wherein estimating the backscatter coefficient includes computing logarithm values by computing a logarithm of the frequency spectra ratio values, forming a frequency spectra ratio decay curve by arranging the logarithm values as a function of depth location, computing a y-intercept of the frequency spectra ratio decay curve, and estimating the backscatter coefficient based on the y-intercept of the frequency spectra ratio decay curve.

23. The method as recited in claim 22, wherein arranging the plurality of frequency spectra ratio values as a function of depth location includes providing transducer response data to the computer system, computing a transducer response ratio, and weighting the plurality of frequency spectra ratio values based on the transducer response ratio.

24. The method as recited in claim 23, further comprising computing a slope of the frequency spectra ratio decay curve and estimating an attenuation coefficient value based on the slope.

25. The method as recited in claim 1, wherein the first frequency is spectrally adjacent to the second frequency.

* * * * *